United States Patent
Fuller et al.

(10) Patent No.: US 7,402,654 B2
(45) Date of Patent: Jul. 22, 2008

(54) PHI 15 DNA POLYMERASE

(75) Inventors: Carl W. Fuller, Berkeley Heights, NJ (US); Cuong Lam, Piscataway, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 39 days.

(21) Appl. No.: 11/315,390

(22) Filed: Dec. 22, 2005

(65) Prior Publication Data

US 2006/0147967 A1     Jul. 6, 2006

Related U.S. Application Data

(60) Provisional application No. 60/640,914, filed on Dec. 30, 2004.

(51) Int. Cl.
*A61K 38/00* (2006.01)
*C12Q 1/68* (2006.01)
*C07K 1/00* (2006.01)

(52) U.S. Cl. .......................... 530/324; 514/2; 530/350; 435/6

(58) Field of Classification Search ....................... None
See application file for complete search history.

(56) References Cited

FOREIGN PATENT DOCUMENTS

WO    WO 02/086088    10/2002

OTHER PUBLICATIONS

Paces, V., et al., "Nucleotide Sequence of the Major Early Region of Bacillus-Subtilis Phage PZA a Close Relative of PHI-29", Gene (Amsterdam), vol. 38, No. 1-3, 1985, pp. 45-56 & EBI Accession No. Uniprot:P06950.

Nelson, J., "PHI29 DNA Polyermase-Based Methods for Genomic Applications", Journal of Clinical Ligand Assay, Clinical Ligand Assay Society, Wayne, MI, US, vol. 25, No. 3, Oct. 2002, pp. 276-279.

*Primary Examiner*—Cecilia Tsang
*Assistant Examiner*—Maury Audet
(74) *Attorney, Agent, or Firm*—Yonggang Ji

(57) ABSTRACT

A purified recombinant DNA polymerase having high processivity and strand-displacement activity. An isolated nucleic acid that encodes the bacteriophage DNA polymerase. A kit and method for amplifying DNA is also disclosed.

2 Claims, 6 Drawing Sheets

Figure 1

Amino acid sequence of Φ15 DNA polymerase (SEQ ID NO:1)

```
MPRKMYSCDFETTTKVEDCRVWAYGYMNIEDHSEYKIGNSLDEFMSWVLK      50
VQADLYFHNLKFDGAFIINWLERNGFKWSADGLPNTYNTIISRMGQWYMI     100
DICLGYKGKRKIHTVIYDSLKKLPFPVKKIAKDFKLTVLKGDIDYHKERP     150
VGYEITPDEYAYIKNDIQIIAEALLIQFKQGLDRMTAGSDSLKGFKDIIT     200
TKKFKKVFPTLSLGLDKEVRYAYRGGFTWLNDRFKEKEIGEGMVFDVNSL     250
YPAQMYSRLLPYGEPIVFEGKYVWDEDYPLHIQHIRCEFELKEGYIPTIQ     300
IKRSRFYKGNEYLKSSGGEIADLWVSNVDLELMKEHYDLYNVEYISGLKF     350
KATTGLFKDFIDKWTHIKTTSEGAIKQLAKLMLNSLYGKFASNPDVTGKV     400
PYLKENGALGFRLGEEETKDPVYTPMGVFITAWARYTTITAAQACFDRII     450
YCDTDSIHLTGTEIPDVIKDIVDPKKLGYWAHESTFKRAKYLRQKTYIQD     500
IYMKEVDGKLVEGSPDDYTTIKFSVKCAGMTDKIKKEVTFDNFKVGFSRK     550
MKPKPVQVPGGVVLVDDTFTIK                                 572
```

Figure 2

Nucleotide sequence of Φ15 DNA polymerase gene (SEQ ID NO:2)

```
ATGCCGAGAAAGATGTATAGTTGTGACTTTGAGACAACTACTAAAGTGGA     50
AGACTGTAGGGTATGGGCGTATGGTTACATGAATATAGAAGACCACAGTG    100
AGTACAAGATTGGTAATAGCCTTGACGAATTCATGTCTTGGGTTCTGAAA    150
GTACAAGCTGATCTATATTTCCATAACCTCAAATTTGACGGAGCTTTTAT    200
CATTAACTGGTTAGAACGTAATGGTTTTAAGTGGTCGGCTGACGGATTAC    250
CAAACACATATAATACGATCATATCAAGAATGGGACAATGGTACATGATC    300
GACATATGTTTAGGTTATAAGGGTAAACGCAAGATACATACAGTGATTTA    350
TGACAGCTTAAAGAAATTGCCGTTCCCTGTTAAAAAGATAGCCAAGGACT    400
TTAAACTTACTGTTCTCAAAGGTGACATTGATTACCATAAAGAAAGACCA    450
GTCGGCTATGAGATAACACCCGATGAATACGCCTATATTAAAAACGATAT    500
TCAGATTATTGCAGAAGCTCTGTTAATTCAGTTTAAACAAGGTTTAGACC    550
GGATGACAGCAGGTAGTGATAGTCTAAAGGGATTTAAAGATATTATAACC    600
ACCAAGAAATTTAAAAAGGTATTTCCTACACTGAGCCTTGGGCTTGATAA    650
GGAAGTTAGATACGCATATAGAGGCGGTTTTACATGGTTAAATGATCGTT    700
TCAAAGAAAAGAAATCGGAGAAGGCATGGTCTTTGATGTTAATAGCCTA    750
TATCCTGCACAGATGTATAGCCGTCTCCTTCCATATGGTGAACCTATAGT    800
ATTCGAGGGTAAATACGTTTGGGACGAAGATTACCCACTACACATACAGC    850
ATATCAGATGTGAGTTCGAATTGAAAGAGGGCTATATACCTACTATACAG    900
ATAAAAGGAGTAGGTTTTATAAAGGCAATGAGTACCTAAAGAGTAGCGG    950
CGGTGAGATAGCTGATCTCTGGGTGTCGAATGTAGACCTAGAATTAATGA   1000
AAGAGCATTATGATTTGTATAACGTTGAGTATATCAGTGGCTTAAAATTT   1050
AAAGCAACTACAGGGCTGTTTAAAGATTTTATAGATAAATGGACACATAT   1100
TAAGACGACATCAGAAGGAGCGATAAAGCAACTAGCAAAACTGATGTTAA   1150
ATAGTCTATATGGTAAATTCGCTAGTAACCCTGATGTTACAGGTAAAGTC   1200
CCTTATTTAAAAGAGAACGGGGCGCTAGGATTCAGACTTGGAGAAGAGGA   1250
AACAAAAGACCCTGTTTATACACCTATGGGCGTTTTCATCACTGCATGGG   1300
CTAGATACACGACAATTACAGCGGCACAGGCATGTTTTGATCGGATAATA   1350
```

Figure 2 (continued)

```
TACTGTGATACTGACAGCATACATTTAACGGGGACAGAGATACCCGACGT  1400
AATAAAAGATATAGTTGACCCTAAGAAGTTGGGGTATTGGGCACATGAAA  1450
GCACGTTTAAAAGAGCTAAATATCTGAGGCAGAAGACCTATATACAGGAC  1500
ATCTATATGAAAGAAGTAGATGGTAAGTTAGTTGAGGGAAGTCCAGATGA  1550
TTATACTACTATAAAATTTAGTGTTAAATGTGCCGGGATGACTGACAAGA  1600
TTAAGAAAGAGGTTACTTTTGATAATTTCAAGGTTGGTTTTAGTCGGAAA  1650
ATGAAGCCTAAGCCTGTGCAAGTGCCGGGCGGGGTGGTTCTGGTTGATGA  1700
CACATTCACGATCAAATAA                                 1719
```

PHI 15 DNA POLYMERASE

CROSS-REFERENCE TO RELATED APPLICATIONS

This application claims priority to U.S. provisional patent application No. 60/640,914 filed Dec. 30, 2004; the entire disclosure of which is incorporated herein by reference in its entirety.

BACKGROUND OF THE INVENTION

1. Field of the Invention

This invention relates to a DNA polymerase suitable for DNA amplification. More specifically, this invention related to a bacteriophage Φ15 DNA polymerase having strand-displacement activity.

2. Description of Related Art

DNA sequencing involves the generation of four populations of single-stranded DNA fragments, having one defined terminus and one variable terminus. The variable terminus always terminates at a specific given nucleotide base (either guanine (G), adenine (A), thymine (T), or cytosine (C)). The four different sets of fragments are each separated on the basis of their length, on a high resolution polyacrylamide gel; each band on the gel corresponds colinearly to a specific nucleotide in the DNA sequence, thus identifying the positions in the sequence of the given nucleotide base.

Generally there are two methods of DNA sequencing. One method (Maxam and Gilbert sequencing) involves the chemical degradation of isolated DNA fragments, each labeled with a single radiolabel at its defined terminus, each reaction yielding a limited cleavage specifically at one or more of the four bases (G, A, T or C). This method generally requires no DNA polymerase and has lost popularity as the other, dideoxy sequencing method has become improved in many ways over the past 25 years.

The second method (dideoxy sequencing) involves the enzymatic synthesis of a DNA strand. Four separate syntheses are run, each reaction being caused to terminate at a specific base (G, A, T or C) via incorporation of the appropriate chain terminating dideoxynucleotide. The latter method is preferred since the DNA fragments are uniformly labelled (instead of end labelled) and thus the larger DNA fragments contain increasingly more radioactivity. Further, $^{35}S$-labelled nucleotides can be used in place of $^{32}P$-labelled nucleotides, resulting in sharper definition; and the reaction products are simple to interpret since each lane corresponds only to either G, A, T or C. The enzymes used for most dideoxy sequencing is the *Escherichia coli* DNA-polymerase I large fragment ("Klenow"), AMV reverse transcriptase, and T7 DNA polymerase (Tabor et al., U.S. Pat. No. 4,795,699). The T7 DNA polymerase used for sequencing is said to be advantageous over other DNA polymerases because it is processive, has no associated exonuclease activity, does not discriminate against nucleotide analog incorporation, and can utilize small oligonucleotides as primers. These properties are said to make the polymerase ideal for DNA sequencing. Id.

A means of amplifying target DNA molecules is of value because such amplified DNA is frequently used in subsequent analysis methods including DNA sequencing, cloning, mapping, genotyping, generation of probes, and diagnostic testing.

There are several established methods that permit amplification of nucleic acids. Most of these methods were designed around the amplification of selected or specific DNA targets using specific probes or primers. Examples include the polymerase chain reaction (PCR), ligase chain reaction (LCR), self-sustained sequence replication (3SR), nucleic acid sequence based amplification (NASBA), strand displacement amplification (SDA), and amplification with Q.βreplicase (Birkenmeyer and Mushahwar, J. Virological Methods, 35:117-126 (1991); Landegren, Trends Genetics, 9:199-202 (1993)).

In addition, several methods have been employed to amplify circular DNA molecules such as plasmids or DNA from bacteriophage such as M13. One (cloning) is simply the propagation of these molecules in suitable host strains of *E. coli*, followed by isolation of the DNA by well-established protocols (Sambrook, J., Fritsch, E. F., and Maniatis, T. Molecular Cloning, A Laboratory Manual, 1989, Cold Spring Harbor Laboratory Press, Cold Spring Harbor, N.Y.). PCR has also been a frequently used method to amplify defined sequences in DNA targets such as plasmids or DNA from bacteriophage such as M13 (PCR Protocols, 1990, Ed. M. A. Innis, D. H. Gelfand, J. J. Sninsky, Academic Press, San Diego.) Some of these methods suffer from being laborious, expensive, time-consuming, inefficient, and lacking in sensitivity.

As an improvement on these methods, linear rolling circle amplification (LRCA) uses a primer annealed to a circular target DNA molecule and DNA polymerase is added. The amplification target circle (ATC) acts as a template on which new DNA is made, with the polymerase extending the primer as a continuous strand. Once the polymerase has completed a full circuit of the template, it displaces the product strand and continues copying the template forming a series of repeats of the sequence complementary to the circle. This process can generate hundreds or even thousands of copies of the template during several hours of reaction, with the number of copies increasing linearly (not accelerating) with time. An improvement on LRCA is exponential RCA (ERCA). To achieve exponential or accelerating amplification, an additional primer that anneals to the replicated complementary strand is provided. This creates new centers of amplification on the product strand, thereby providing accelerating, exponential kinetics and increased amplification. Exponential rolling circle amplification (ERCA) employs a cascade of strand displacement reactions, also referred to as HRCA (Lizardi, P. M. et al. Nature Genetics, 19, 225-231 (1998)). However, ERCA is limited to the use of just a single primer annealed to the circular DNA target molecule, and a single primer for the product strand. Another limitation is that one needs to know a specific DNA sequence within the circular target sequence in order to make the primers. Furthermore, the circular DNA target molecule must be a circle that is nicked or at least partially single-stranded.

Another method (referred to herein as Multiply-Primed Rolling Circle Amplification—MPRCA) that avoids some of these disadvantages employs multiple specific primers to perform rolling circle amplification by using multiple primers for the amplification of individual target circles. This has the advantage of more rapid synthesis with multiple growing points on each circular template molecule. Amplification can be linear if all the primers anneal only to the circular target strand, or exponential if primers are provided for both strands.

The methods provide a mechanism for "in vitro cloning", i.e. without the need for cloning into an organism, of known or unknown target DNAs enclosed in circles. A padlock probe may be used to copy the target sequence into a circle by the gap fill-in method (Lizardi, P. M. et al. Nature Genetics, 19, 225-231 (1998)). Alternatively, target sequences can be copied or inserted into circular ssDNA or dsDNA by many other commonly used methods. The RCA amplification overcomes the need to generate amplified yields of the DNA by cloning in organisms.

While specific target amplification is widely used, general amplification of all the sequences in a target sample can also be useful. This can be achieved with a form of MPRCA in which a collection of primers of arbitrary or random sequence is used. In this way, amplification of a circular target DNA molecule of unknown sequence can be achieved. Another advantage is that the amplification of single-stranded or double-stranded circular target DNA molecules may be carried out isothermally and/or at ambient temperatures. Other advantages include being highly useful in new applications of rolling circle amplification, low cost, sensitivity to low concentration of target circle, flexibility, especially in the use of detection reagents, and low risk of contamination (U.S. Pat. No. 6,323,009; Genomics 2002 Vol. 80, No. 6, 691-8; Biotechniques 2002 June Suppl. 44-47; Genome Research, 2001 Vol. 11 No. 6, 1095-9).

In some embodiments, procedures are employed that improve on the yield of amplified product DNA by using multiple primers that are resistant to degradation by exonuclease activity that may be present in the reaction. This has the advantage of permitting the primers to persist in reactions that contain an exonuclease activity and that may be carried out for long incubation periods. The persistence of primers allows new priming events to occur for the entire incubation time of the reaction, which is one of the hallmarks of ERCA and has the advantage of increasing the yield of amplified DNA.

Random primer RCA also has the benefit of generating double stranded products. This is because the linear ssDNA products generated by copying of the circular template will themselves be converted to duplex form by random priming of DNA synthesis. Double stranded DNA product is advantageous in allowing for DNA sequencing of either strand and for restriction endonuclease digestion and other methods used in cloning, labeling, and detection.

Methods have published for whole genome amplification using degenerate primers (Cheung, V. G. and Nelson, S. F. Proc. Natl. Acad. Sci. USA, 93, 14676-14679 (1996)) and random primers (Zhang, L. et al., Proc. Natl. Acad. Sci. USA, 89, 5847-5851 (1992)) where a subset of a complex mixture of targets such as genomic DNA is amplified. Reduction of complexity is an objective of these methods.

It has been found, however, that the use of the DNA polymerase from bacteriophage Φ29 (PHI29) along with random sequence hexamer primers is particularly advantageous for general amplification of circular DNA sequences by exponential MPRCA mechanism. In addition, it has also been found that this combination is also effective in amplification of linear DNA molecules in a process termed MDA for Multiple Displacement Amplification. It is capable of amplification of the 50 kb chromosome of bacteriophage λ, or of larger linear molecules such as isolated human chromosomal DNA. This method makes use of the unusual properties of Φ29 DNA polymerase, namely high processivity and ability to displace a strand annealed to the template strand during synthesis—so called strand-displacement activity (Proc Natl Acad Sci USA. 2005 May 3;102(18):6407-12). Most DNA polymerases slow or stop when they encounter a strand annealed to the template but Φ29 DNA polymerase has the same synthesis rate on single-stranded DNA as when it must displace a strand from a double-stranded template. Also, most DNA polymerases remain bound to a template strand long enough to polymerize only a few nucleotides up to about 1000 nucleotides. Synthesis at that particular site then stops as the polymerase un-binds, and synthesis will only resume when another molecule of polymerase binds later. In contrast, Φ29 DNA polymerase appears to bind long enough to polymerize many thousands of nucleotides without stopping, extending synthesis over wide stretches of template sequence. Together, these unique properties of Φ29 DNA polymerase make it particularly effective for MDA and MPRCA using random-sequence primers such as hexamers.

Experiments using a variety of DNA polymerases have revealed that many of these enzymes do not support amplification by MDA. This is presumably because these enzymes will slow or stop whenever they encounter a double-stranded region of the template DNA such as a region already copied by synthesis on single-stranded template. Thus, synthesis stops when all of the single-stranded DNA in the sample is converted to double stranded DNA. This limits amplification to 2-fold at most while the Φ29 DNA polymerase readily amplifies DNA one million-fold or more.

New polymerases are desirable. This need is addressed in greater detail below.

SUMMARY OF THE INVENTION

This invention relates to isolation and purification of a new DNA polymerase from bacteriophage Φ15 and using it for amplification of DNA. DNA amplification involves annealing primers to strands of DNA sequence and incubating the annealed mixture with the DNA polymerase isolated from bacteriophage Φ15.

BRIEF DESCRIPTION OF DRAWINGS

FIG. 1 is the Amino acid sequence of Φ15 DNA polymerase (SEQ ID NO:1).

FIG. 2 is the nucleotide sequence of the Φ15 DNA polymerase gene (SEQ ID NO:2).

DETAILED DESCRIPTION OF THE INVENTION

Figure 3:
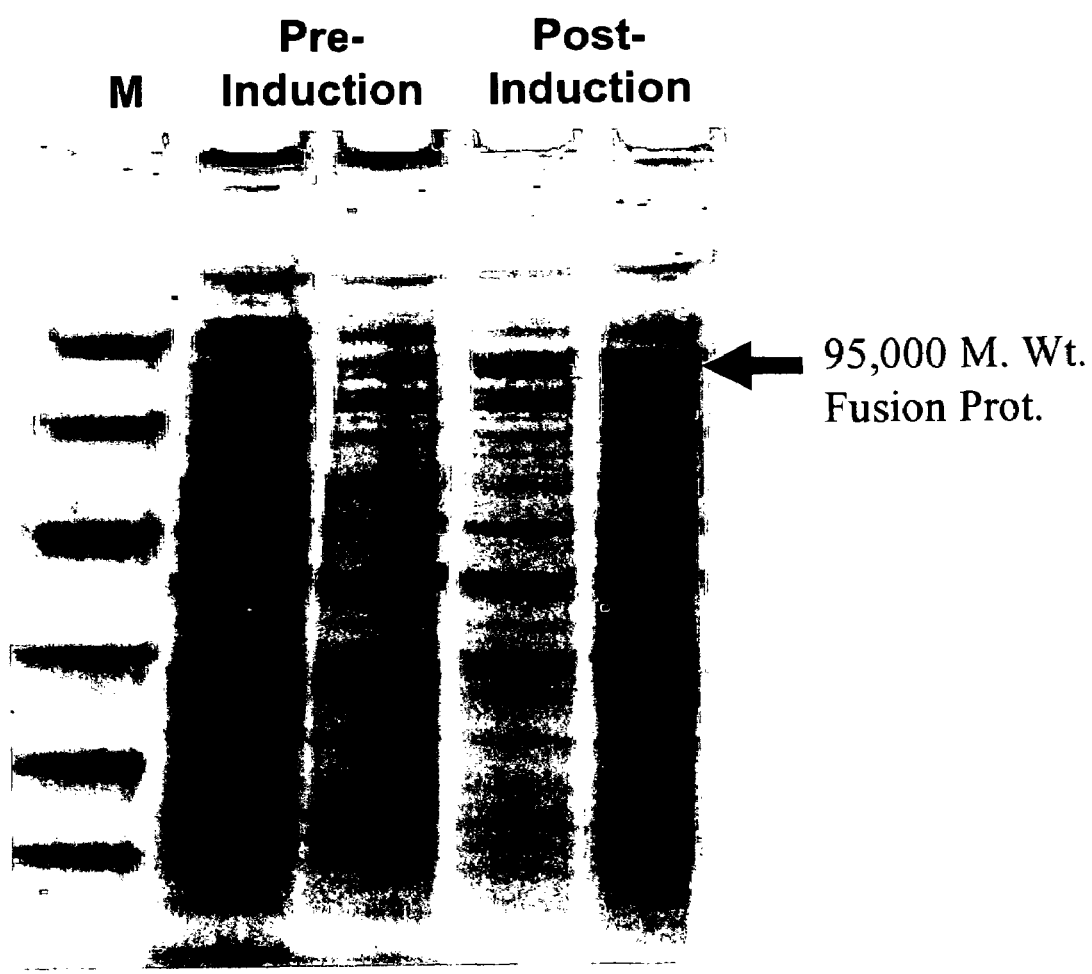
FIG. 3 is an SDS electrophoresis experiment showing induction of a new protein in cells containing a clone of the bacteriophage Φ15 DNA polymerase gene. The induced protein is a fusion of polymerase with glutathione S-transferase.

The instant disclosure teaches a purified recombinant DNA polymerase comprising the amino acid sequence set forth in FIG. 1. The instant disclosure also teaches an isolated nucleic acid that encodes a DNA polymerase, wherein said nucleic acid comprises of the nucleotide sequence set forth in FIG. 2. It is also contemplated that variant nucleic acids may also encode for the DNA polymerase with the amino acid sequence set forth in FIG. 1.

The instant disclosure also teaches methods of sequencing and amplifying DNA with the DNA polymerase and a kit for sequencing and amplifying DNA comprising the DNA polymerase.

In a first aspect, the invention features a Φ15 DNA polymerase, which is a Φ29-type DNA polymerase.

A Φ29-type DNA polymerase as used herein means any DNA polymerase isolated from the related phages which contain a terminal protein used in the initiation of replication of DNA. These phages are generally described by Salas, in *The Bacteriophages* 169, 1988. These phages are closely related in the structure of their chromosomes and in some cases the sequence of their DNA polymerases, some differing by as few as 6 amino acid changes with 5 of those amino acids being replaced by similar amino acids. These phages have a short inverted terminal repeat sequence of length between about 6 and 300 nucleotides. These polymerases have a highly active 3'-5' exonuclease activity, but no 5'-3' exonuclease activity.

Bacteriophage Φ29 DNA polymerase is a member of the T4 or type-B family of DNA polymerases, not the type-A family that includes DNA polymerase I of *E. coli*, Taq, and bacteriophage T7. Polymerases of this T4 family (Gene. 1992 Mar. 1;112(1):139-44) are typically able to recognize chain terminating agents such as dideoxynucleotides and therefore are potentially useful for DNA sequencing although generally less so than, for example bacteriophage T7 DNA polymerase.

In general, a DNA polymerase of this invention is processive. The polymerase also has a strand-displacement activity.

By processive is meant that the DNA polymerase is able to continuously incorporate nucleotides using the same primer template, without dissociating from either or both the primer or the template molecules, under conditions normally used for DNA synthesis reactions, or other primer extension reactions.

The ability of the polymerases of this invention to produce strand displacement is advantageous in this invention because, in combination with processivity, it allows synthesis of long DNA molecules of at least 70 kb, or even greater. Strand displacement activity is measured by any standard technique, for example, a polymerase may be incubated in a mixture with a single-stranded circular DNA molecule (e.g., M13) and a primer. If DNA molecules of length greater than the original circular molecule are synthesized, then the polymerase is able to displace DNA strands of a double-stranded molecule and continue to synthesize DNA—thus, it has a strand displacement activity. Such activity may be present in a single protein molecule, and may not require energy in the form of ATP or its equivalent, utilizing only the standard deoxynucleoside triphosphates required to synthesize DNA. This activity is also observed when DNA synthesis is initiated by a terminal protein.

The DNA polymerase of this invention is useful for PCR and DNA amplification.

One embodiment of the invention relates to an isolated DNA polymerase polypeptide comprising an amino acid sequence selected from the group consisting of: (a) the amino acid sequence of SEQ ID NO:1; (b) a fragment of at least 8 amino acids of SEQ ID NO:1; (c) an isolated polypeptide according to (a) or (b) in which at least 95% of deviations from the sequence of (a) or (b) are conservative substitutions; and (d) an isolated polypeptide having at least 65% amino acid sequence identity to the isolated polypeptide of (a) or (b).

Another embodiment of the invention related to an isolated polypeptide produced by a method comprising: culturing a host cell, or the progeny thereof, transformed to contain the nucleic acid molecule of any one of (i) the nucleotide sequence of SEQ ID NO:2, (ii) a nucleotide sequence that is a degenerate variant of the nucleotide sequence of SEQ ID NO:2, (iii) a nucleotide sequence that encodes a polypeptide with the amino acid sequence of SEQ ID NO:1, (iv) a nucleotide sequence that encodes a polypeptide with the amino acid sequence of SEQ ID NO:1 with conservative amino acid substitutions; (v) a nucleotide sequence that encodes a polypeptide with the amino acid sequence of SEQ ID NO:1 with moderately conservative amino acid substitutions, or (vi) a nucleotide sequence that is the complement of the nucleotide sequence of any one of (i)-(v), under conditions in which the protein encoded by the nucleic acid molecule is expressed.

The invention also relates to an isolated nucleic acid encoding a polypeptide having DNA polymerase activity. Therefore, one embodiment of the invention relates to an isolated nucleic acid comprising: a polynucleotide having a sequence selected from the group consisting of (i) the nucleotide sequence of SEQ ID NO:2; (ii) a nucleotide sequence that is a degenerate variant of the nucleotide sequence of SEQ ID NO:2; (iii) a nucleotide sequence at least 90% identical in sequence to SEQ ID NO:2, (iv) a nucleotide sequence that encodes a polypeptide with the amino acid sequence of SEQ ID NO:1, (v) a nucleotide sequence that encodes a polypeptide at least 90% identical in sequence to SEQ ID NO:1, and (vi) a nucleotide sequence that is the complete complement of the nucleotide sequence of any one of (i)-(v), wherein the nucleic acid encodes a polypeptide having DNA polymerase activity.

Another embodiment of the invention relates to an isolated nucleic acid comprising: a polynucleotide having a sequence selected from the group consisting of (i) the nucleotide sequence of SEQ ID NO:2, (ii) a nucleotide sequence that is a degenerate variant of the nucleotide sequence of SEQ ID NO:2, (iii) a nucleotide sequence at least 95% identical in sequence to SEQ ID NO:2, (iv) a nucleotide sequence that encodes a polypeptide with the amino acid sequence of SEQ ID NO:1, (v) a nucleotide sequence that encodes a polypeptide at least 95% identical in sequence to SEQ ID NO:1, and (vi) a nucleotide sequence that is the complete complement of the nucleotide sequence of any one of (i)-(v), wherein the nucleic acid encodes a polypeptide having DNA polymerase activity.

Yet another embodiment of the invention relates to an isolated nucleic acid comprising: a polynucleotide having a sequence selected from the group consisting of (i) the nucleotide sequence of SEQ ID NO:2, (ii) a nucleotide sequence that is a degenerate variant of the nucleotide sequence of SEQ ID NO:2, (iii) a nucleotide sequence at least 99% identical in sequence to SEQ ID NO:2, (iv) a nucleotide sequence that encodes a polypeptide with the amino acid sequence of SEQ ID NO:1, (v) a nucleotide sequence that encodes a polypeptide at least 99% identical in sequence to SEQ ID NO:1, and (vi) a nucleotide sequence that is the complete complement of the nucleotide sequence of any one of (i)-(v), wherein the nucleic acid encodes a polypeptide having DNA polymerase activity.

The invention also relates to a replicable vector comprising the isolated nucleic acid, as well as an expression vector comprising the isolated nucleic acid. The invention further relates to host cells transformed to contain the replicable vector of, or the progeny thereof containing the replicable vector, and host cells transformed to contain the expression vector, or the progeny thereof containing the expression vector.

The invention further provides a method for producing a DNA polymerase polypeptide, the method comprising: culturing the host cell containing the expression vector comprising the isolated nucleic acid under conditions in which the polypeptide encoded by said nucleic acid is expressed, and isolating the expressed protein.

In a related aspect, the invention features a kit for DNA sequencing or amplification, including a supply of Φ15 DNA polymerase. By kit is meant a container designed to keep the components separated from each other, preferably in condition for use in a DNA sequencing or amplification reactions. Optionally, the kit further includes a set of random-sequence primers. Preferably, the primers are of length 4-10 nucleotides. Most preferably, the primers are hexamers. Also preferably, the primers are nuclease resistant.

In another aspect, the invention features a method for amplification of a DNA sequence. The method includes a polymerase reaction of a nucleic acid template, a primer, a nucleic acid polymerase, and at least one nucleoside polyphosphate, the improvement comprises conducting the polymerase reaction using the Φ15 DNA polymerase. Amplification is achieved by rolling circle amplification (RCA), strand displacement amplification (SDA) or nucleic acid sequence based amplification (NASBA).

The invention is further described by reference to the examples below.

EXAMPLES

The following examples illustrate certain preferred embodiments of the instant invention but are not intended to be illustrative of all embodiments. These examples should not be construed as limiting the appended claims and/or the scope of this invention.

Example 1

Cloning the Gene for Φ15 DNA Polymerase Expression

Bacteriophage Φ15 is an organism related to bacteriophage Φ29 (J. Mol. Evol. 1999, 48:197-208). Like the other bacteriophage in this group, it features a DNA chromosome of about 20 kb with protein attached to the 5' ends, and many similarities in genome organization. The gene encoding Φ15 DNA polymerase was first amplified from phage DNA by PCR using the following two primers:

```
CKL&PCRp15H1primer (BamHI site underlined,
SEQ ID NO:3):
5' GGG ATC CCC GAG AAA GAT GTA TAG TTG TGA C 3'
and CKL&PCRp15XhoIprimer (XhoI site underlined,
SEQ ID NO:4):
5' AAC TCG AGG GTT ATT TGA TTG TGA ATG TGT CAT C 3'
```

The sequence of the BamHI primer was chosen to eliminate the original ATG codon at the 5' terminus of the coding sequence to improve the rate of expression of the fused polymerase-GST protein. The PCR process was carried out using Pfu DNA polymerase using standard reaction conditions for this enzyme. The resulting 1.8 kb product purified using glass fiber filter adsorption and was cut with a combination of BamHI and XhoI as was the cloning vector pGEX-6P-2 (GE Healthcare), a vector that is designed to fuse the protein of interest (DNA polymerase) with GST (Glutathione S-Transferase). The digested DNAs were ligated and used to transform E. coli DH5α. Several of the resulting colonies were checked for having correct-sized inserts (1.8 kb), and one was chosen to transform E. coli strain JM109. This was used for sequencing and for enzyme expression.

Example 2

Expression and Purification of Φ15 DNA Polymerase

The fusion-protein clone was grown in 2L of 2× YT medium until the O.D. at 600 nm reached 1.5. Then IPTG (isopropylthiogalactoside) was added to a final concentration of 1 mM to induce expression from the plasmid. Growth was continued for an additional 2 hours, then the culture was chilled, and the cells harvested yielding 8.8 g of cell paste. Samples taken pre- and post-induction were submitted to SDS gel electrophoresis analysis (FIG. 3) that indicated induction of a new protein species of about 95,000 molecular weight as expected for the fusion of the 66,000 polymerase and 30,000 GST.

Next, the cell paste was suspended in 30 ml of ice cold PBS buffer with 2 mM DTT and 2 mM PMSF (phenylmethylsulfonylfluoride). The cells were disrupted using an Avestin EmulsiFlex™ homogenizer using 3 passes at ~15,000 psi. Then nonionic detergent NP-40 was added to a final concentration of 1% (v/v) and the suspension shaken gently for 30 min. at 4° C. Debris was removed by centrifugation at 2,000 rpm for 30 min. and the supernatant shaken with glutathione Sepharose 4B (10 ml) overnight at 4° C. to bind the fusion protein to the affinity resin.

Figure 4:
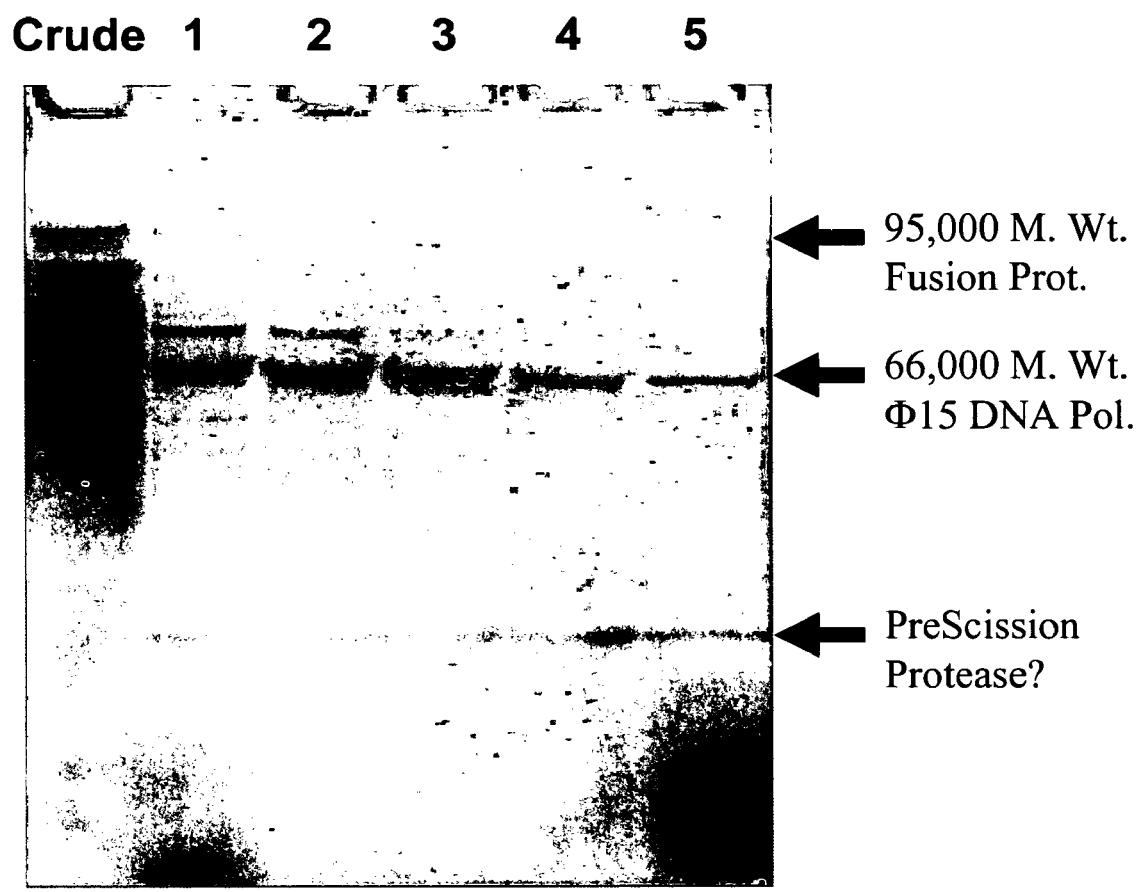
FIG. 4 is an SDS electrophoresis experiment showing purification of Φ15 DNA polymerase.

The Sepharose with any bound protein was then packed into a column and the resin washed with 5 column volumes of buffer (PBS buffer with 1% NP-40, 2 mM DTT and 2 mM PMSF). Then the fusion protein bound to the column was digested with PreScission™ protease (GE Healthcare) following the manufacturer's instructions for 4 hours at 4° C. Then the cleaved protein was eluted with 50 mM Tris pH 7.0, 1 mM EDTA and 300 mM NaCl, collecting 1 ml fractions. Samples from the fractions were analyzed by SDS gel electrophoresis, revealing highly purified protein with a molecular weight of 66,000, consistent with the expected polymerase molecular weight (FIG. 4). While all the fractions appear to have a small amount of protease remaining in them (<5%), the purest fractions starting with number 3 were used for further testing.

Example 3

Activity of Φ15 DNA Polymerase

The DNA polymerase activity of the purified Φ15 DNA polymerase fraction was compared with that of purified Φ29 DNA polymerase using radiochemical polymerase assays. Each assay reaction mixture (50 μl) contained 2 μg pUC18 DNA, 2 nmol random-sequence hexamer primer (denatured by heating to 97° C., 12 min, then cooling on ice), 0.2 mM each dNTP (including $\alpha^{33}$P dCTP) and indicated amounts of diluted polymerase. Reactions were incubated at 30° C. for 30 minutes, and then acid-insoluble radioactivity measured by precipitating with trichloroacetic acid. This assay parallels the reaction conditions used for MDA and MPRCA (U.S. Pat. No. 6,323,009) so it will reflect activity in these applications.

Figure 5:
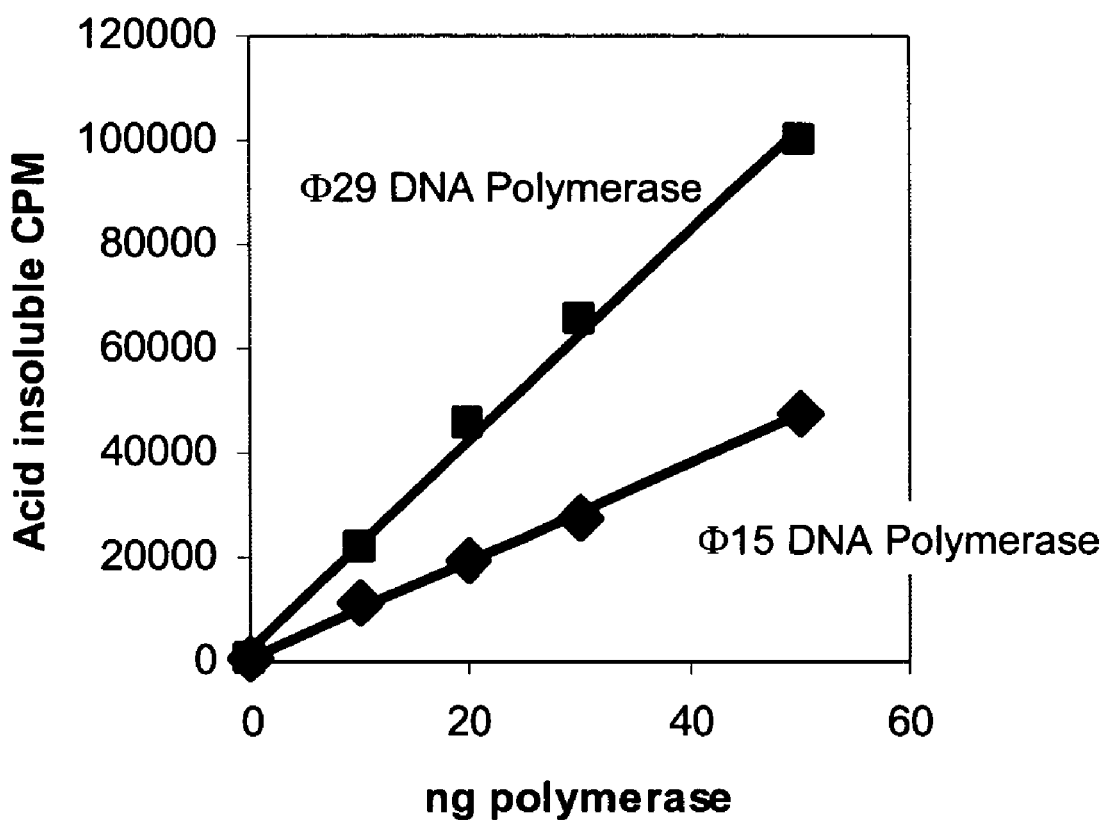
FIG. 5 shows a DNA polymerase assay comparing specific activity of purified Φ15 DNA polymerase with that of purified Φ29 DNA polymerase.

Using this assay, the specific activity of the Φ15 DNA polymerase measures 50-65% that of highly purified Φ29 DNA polymerase (FIG. 5). This demonstrates that the protein isolated is indeed a highly active DNA polymerase.

Those skilled in the art having the benefit of the teachings of the present invention as set forth above, can effect numerous modifications thereto. These modifications are to be construed as being encompassed within the scope of the present invention as set forth in the appended claims.

What is claimed is:

1. An isolated polypeptide comprising the amino acid sequence of SEQ ID NO:1, wherein said isolated polypeptide has DNA polymerase activity.

2. An isolated polypeptide of claim 1, wherein said polypeptide is encoded by the nucleic acid sequence of SEQ ID NO:2.

* * * * *

SEQUENCE LISTING

<160> NUMBER OF SEQ ID NOS: 4

<210> SEQ ID NO 1
<211> LENGTH: 572
<212> TYPE: PRT
<213> ORGANISM: Bacteriophage phi-15

<400> SEQUENCE: 1

```
Met Pro Arg Lys Met Tyr Ser Cys Asp Phe Glu Thr Thr Lys Val
 1               5                  10                  15

Glu Asp Cys Arg Val Trp Ala Tyr Gly Tyr Met Asn Ile Glu Asp His
                20                  25                  30

Ser Glu Tyr Lys Ile Gly Asn Ser Leu Asp Glu Phe Met Ser Trp Val
                35                  40                  45

Leu Lys Val Gln Ala Asp Leu Tyr Phe His Asn Leu Lys Phe Asp Gly
            50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                    85                  90                  95

Trp Tyr Met Ile Asp Ile Cys Leu Gly Tyr Lys Gly Lys Arg Lys Ile
                100                 105                 110

His Thr Val Ile Tyr Asp Ser Leu Lys Lys Leu Pro Phe Pro Val Lys
                115                 120                 125

Lys Ile Ala Lys Asp Phe Lys Leu Thr Val Leu Lys Gly Asp Ile Asp
        130                 135                 140

Tyr His Lys Glu Arg Pro Val Gly Tyr Glu Ile Thr Pro Asp Glu Tyr
145                 150                 155                 160

Ala Tyr Ile Lys Asn Asp Ile Gln Ile Ile Ala Glu Ala Leu Leu Ile
                165                 170                 175

Gln Phe Lys Gln Gly Leu Asp Arg Met Thr Ala Gly Ser Asp Ser Leu
                180                 185                 190

Lys Gly Phe Lys Asp Ile Ile Thr Thr Lys Lys Phe Lys Lys Val Phe
            195                 200                 205

Pro Thr Leu Ser Leu Gly Leu Asp Lys Glu Val Arg Tyr Ala Tyr Arg
210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
                260                 265                 270

Val Trp Asp Glu Asp Tyr Pro Leu His Ile Gln His Ile Arg Cys Glu
            275                 280                 285

Phe Glu Leu Lys Glu Gly Tyr Ile Pro Thr Ile Gln Ile Lys Arg Ser
        290                 295                 300

Arg Phe Tyr Lys Gly Asn Glu Tyr Leu Lys Ser Ser Gly Gly Glu Ile
305                 310                 315                 320

Ala Asp Leu Trp Val Ser Asn Val Asp Leu Glu Leu Met Lys Glu His
                325                 330                 335

Tyr Asp Leu Tyr Asn Val Glu Tyr Ile Ser Gly Leu Lys Phe Lys Ala
                340                 345                 350

Thr Thr Gly Leu Phe Lys Asp Phe Ile Asp Lys Trp Thr His Ile Lys
```

|                     355                     360                     365          |
|---|

Thr Thr Ser Glu Gly Ala Ile Lys Gln Leu Ala Lys Leu Met Leu Asn
    370                     375                     380

Ser Leu Tyr Gly Lys Phe Ala Ser Asn Pro Asp Val Thr Gly Lys Val
385                     390                     395                     400

Pro Tyr Leu Lys Glu Asn Gly Ala Leu Gly Phe Arg Leu Gly Glu Glu
                    405                     410                     415

Glu Thr Lys Asp Pro Val Tyr Thr Pro Met Gly Val Phe Ile Thr Ala
                    420                     425                     430

Trp Ala Arg Tyr Thr Thr Ile Thr Ala Ala Gln Ala Cys Phe Asp Arg
                    435                     440                     445

Ile Ile Tyr Cys Asp Thr Asp Ser Ile His Leu Thr Gly Thr Glu Ile
            450                     455                     460

Pro Asp Val Ile Lys Asp Ile Val Asp Pro Lys Lys Leu Gly Tyr Trp
465                     470                     475                     480

Ala His Glu Ser Thr Phe Lys Arg Ala Lys Tyr Leu Arg Gln Lys Thr
                    485                     490                     495

Tyr Ile Gln Asp Ile Tyr Met Lys Glu Val Asp Gly Lys Leu Val Glu
                    500                     505                     510

Gly Ser Pro Asp Asp Tyr Thr Thr Ile Lys Phe Ser Val Lys Cys Ala
                    515                     520                     525

Gly Met Thr Asp Lys Ile Lys Lys Glu Val Thr Phe Asp Asn Phe Lys
                    530                     535                     540

Val Gly Phe Ser Arg Lys Met Lys Pro Lys Pro Val Gln Val Pro Gly
545                     550                     555                     560

Gly Val Val Leu Val Asp Asp Thr Phe Thr Ile Lys
                    565                     570

<210> SEQ ID NO 2
<211> LENGTH: 1719
<212> TYPE: DNA
<213> ORGANISM: Bacteriophage phi-15

<400> SEQUENCE: 2

```
atgccgagaa agatgtatag ttgtgacttt gagacaacta ctaaagtgga agactgtagg    60
gtatgggcgt atggttacat gaatatagaa gaccacagtg agtacaagat tggtaatagc   120
cttgacgaat tcatgtcttg ggttctgaaa gtacaagctg atctatattt ccataacctc   180
aaatttgacg gagcttttat cattaactgg ttagaacgta atggttttaa gtggtcggct   240
gacggattac caaacacata taatacgatc atatcaagaa tgggacaatg gtacatgatc   300
gacatatgtt taggttataa gggtaaacgc aagatacata cagtgattta tgacagctta   360
aagaaattgc cgttccctgt taaaaagata gccaaggact ttaaacttac tgttctcaaa   420
ggtgacattg attaccataa agaaagacca gtcggctatg agataacacc cgatgaatac   480
gcctatatta aaacgatat tcagattatt gcagaagctc tgttaattca gtttaaacaa   540
ggtttagacc ggatgacagc aggtagtgat agtctaaagg gatttaaaga tattataacc   600
accaagaaat ttaaaaaggt atttcctaca ctgagccttg gcttgataa ggaagttaga   660
tacgcatata gaggcggttt acatggttta atgatcgtt tcaaagaaaa agaaatcgga   720
gaaggcatgg tctttgatgt taatagccta tatcctgcac agatgtatag ccgtctcctt   780
ccatatggtg aacctatagt attcgagggt aaatacgttt gggacgaaga ttacccacta   840
cacatacagc atatcagatg tgagttcgaa ttgaaagagg ctatatacc tactatacag   900
```

-continued

```
ataaaaagga gtaggtttta taaaggcaat gagtacctaa agagtagcgg cggtgagata    960
gctgatctct gggtgtcgaa tgtagaccta gaattaatga aagagcatta tgatttgtat   1020
aacgttgagt atatcagtgg cttaaaattt aaagcaacta cagggctgtt taaagatttt   1080
atagataaat ggacacatat taagacgaca tcagaaggag cgataaagca actagcaaaa   1140
ctgatgttaa atagtctata tggtaaattc gctagtaacc ctgatgttac aggtaaagtc   1200
ccttatttaa aagagaacgg ggcgctagga ttcagacttg gagaagagga aacaaaagac   1260
cctgtttata cacctatggg cgttttcatc actgcatggg ctagatacac gacaattaca   1320
gcggcacagg catgttttga tcggataata tactgtgata ctgacagcat acatttaacg   1380
gggacagaga tacccgacgt aataaaagat atagttgacc ctaagaagtt ggggtattgg   1440
gcacatgaaa gcacgtttaa aagagctaaa tatctgaggc agaagaccta tatacaggac   1500
atctatatga aagaagtaga tggtaagtta gttgagggaa gtccagatga ttatactact   1560
ataaaattta gtgttaaatg tgccgggatg actgacaaga ttaagaaaga ggttactttt   1620
gataatttca aggttggttt tagtcggaaa atgaagccta agcctgtgca agtgccgggc   1680
ggggtggttc tggttgatga cacattcacg atcaaataa                          1719

<210> SEQ ID NO 3
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 3
gggatccccg agaaagatgt atagttgtga c                                    31

<210> SEQ ID NO 4
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 4
aactcgaggg ttatttgatt gtgaatgtgt catc                                 34
```